United States Patent [19]
Donofrio

[11] Patent Number: 6,110,103
[45] Date of Patent: Aug. 29, 2000

[54] DISPOSABLE ENDOSCOPE SHEATH

[75] Inventor: William Donofrio, Jacksonville, Fla.

[73] Assignee: Xomed Surgical Products, Inc., Jacksonville, Fla.

[21] Appl. No.: 09/093,619

[22] Filed: Jun. 9, 1998

Related U.S. Application Data

[63] Continuation of application No. 08/071,912, Jun. 3, 1993, abandoned.

[51] Int. Cl.$^7$ ..................................................... A61B 1/015
[52] U.S. Cl. .......................... 600/121; 600/114; 600/157
[58] Field of Search .................................. 600/105, 114, 600/121–125, 128, 133, 153, 155, 156, 157, 158

[56] References Cited

U.S. PATENT DOCUMENTS

| | | |
|---|---|---|
| 4,132,227 | 1/1979 | Ibe . |
| 4,281,646 | 8/1981 | Kinoshita . |
| 4,721,097 | 1/1988 | D'Amelio . |
| 4,741,326 | 5/1988 | Sidall et al. . |
| 4,860,731 | 8/1989 | Matsuura . |
| 4,869,238 | 9/1989 | Opie et al. . |
| 4,878,485 | 11/1989 | Adair . |
| 4,881,523 | 11/1989 | Heckele . |
| 4,973,311 | 11/1990 | Iwakoshi et al. . |
| 4,974,580 | 12/1990 | Anapliotis . |
| 4,991,564 | 2/1991 | Takahashi et al. . |
| 4,991,565 | 2/1991 | Takahashi et al. . |
| 5,050,585 | 9/1991 | Takahashi . |
| 5,154,164 | 10/1992 | Chikama . |
| 5,154,166 | 10/1992 | Chikama . |
| 5,159,919 | 11/1992 | Chikama . |
| 5,225,001 | 7/1993 | Manni et al. . |
| 5,237,984 | 8/1993 | Williams, III et al. . |
| 5,287,845 | 2/1994 | Faul et al. . |
| 5,313,934 | 5/1994 | Wiita et al. . |
| 5,320,091 | 6/1994 | Grossi et al. . |
| 5,400,767 | 3/1995 | Murdoch . |

*Primary Examiner*—John P. Leubecker

[57] ABSTRACT

The disposable endoscope sheath includes a low-profile sleeve member that can accommodate a variety of different endoscope lengths that are longer than the sleeve member. In several embodiments of the invention, the sleeve member includes irrigation channels that do not communicate with an endoscope receiving space. In other embodiments of the invention, irrigation fluid passes through the endoscope receiving space of the sleeve member. In all embodiments of the invention, irrigation fluid that is expelled from the sleeve member can flush surgical debris away from the viewing end of the endoscope. The sleeve member has a generally low profile and does not require continuous suction to halt the expulsion of irrigation fluid from the sheath when the irrigation function is not being used. A brief reverse suction can be used to remove a residual drop of cleaning solution from the viewing end of the sheath.

19 Claims, 4 Drawing Sheets

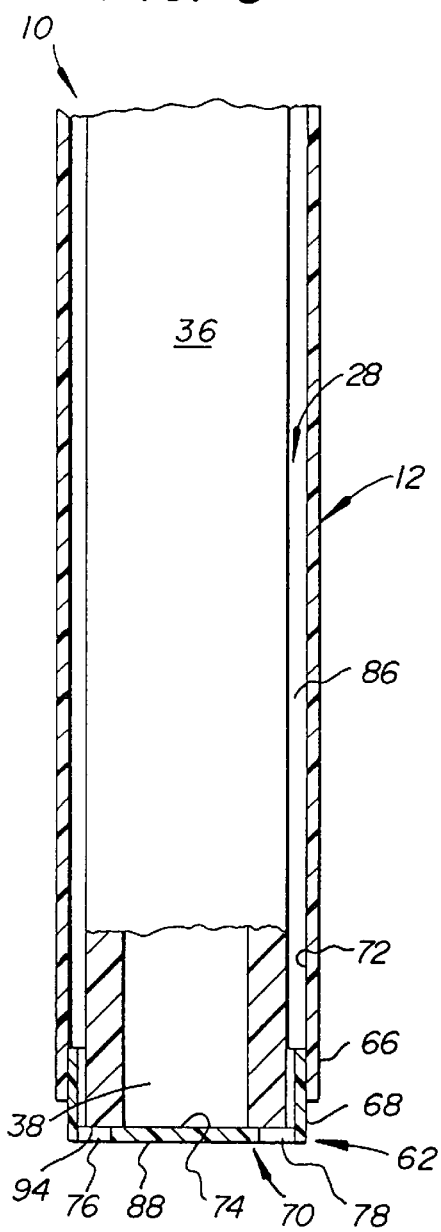
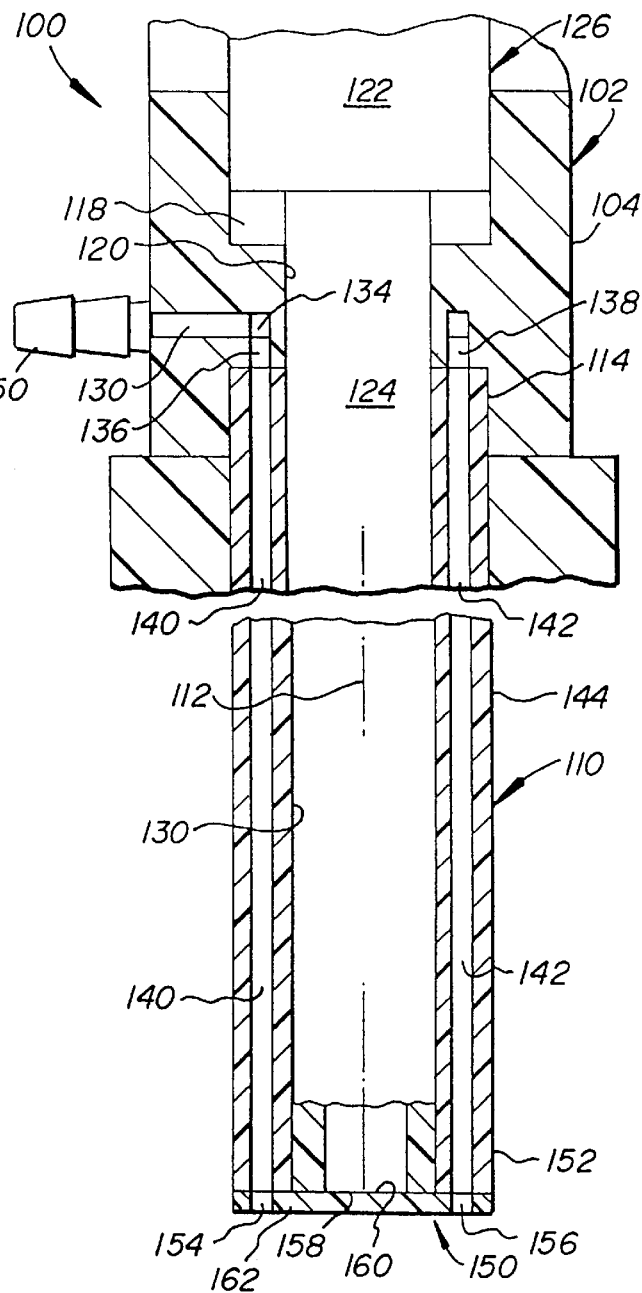
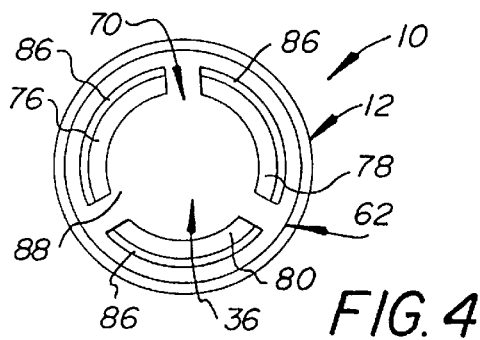
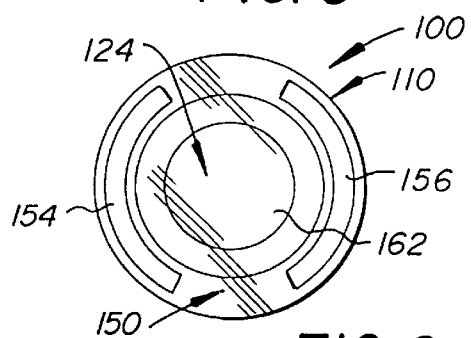

DISPOSABLE ENDOSCOPE SHEATH

This application is a continuation application of application Ser. No. 08/071,912, filed Jun. 3, 1993, now abandoned.

BACKGROUND OF THE INVENTION

This invention is directed to disposable sheaths for endoscopes and more particularly to a low profile disposable sheath that provides effective flushing of surgical debris away from the viewing end of an endoscope.

The term surgical debris is intended to refer to any body material such as blood or tissue that obscures the field of view of an endoscope during surgery.

Endoscopes permit a remote visual view of a surgical site while a surgical procedure is being performed. During surgery, blood, tissue or other body material from the surgical site can splatter onto the viewing end of the endoscope and impair the field of view through the endoscope.

In some instances it is necessary to remove the endoscope from the surgical site to clean the viewing end, which usually interrupts and undesirably prolongs a surgical procedure.

Because of the inconvenience of removing and cleaning an endoscope during surgery, some surgeons prefer to use an endoscope with a sheath that has provision for flushing away at the surgical site any surgical debris that obscures the view through the endoscope.

Known endoscope sheaths, such as shown in U.S. Pat. Nos. 4,991,565 and 4,974,580, are generally custom fitted to the endoscope. The sheath often includes air tubes, water tubes and suction tubes to flush away or suction away surgical debris from the viewing end of the endoscope. The irrigation, suction and air tubes on the endoscope sheath can add significant girth to the profile of the endoscope and thus require a relatively large incision to accommodate the sheath with the endoscope.

Since many endoscopes are of different length, a diversity of corresponding sheath lengths are usually required to provide a compatible fit for each different length endoscope. Endoscope sheaths of different length are thus maintained in inventory by suppliers and users to ensure proper match-up with a selected endoscope.

It is thus desirable to provide an endoscope sheath that is adaptable to a variety of different endoscope lengths, can be of low profile, and permits flushing of debris away from the viewing end of the endoscope.

OBJECTS AND SUMMARY OF THE INVENTION

Among the several objects of the invention may be noted the provision of a novel endoscope sheath, a novel low profile disposable endoscope sheath for flushing debris away from the viewing end of an endoscope, a novel disposable endoscope sheath that can be adapted for use with endoscope barrels or shafts of different length, a novel disposable endoscope sheath that enables irrigating fluid to flush surgical debris away from the viewing end of the endoscope without contacting the endoscope, and a novel disposable endoscope sheath that locates an endoscope barrel in a predetermined position in the sheath.

Other objects and features of the invention will be in part apparent and in part pointed out hereinafter.

In accordance with the invention, the disposable sheath for an endoscope includes a sleeve housing or collar that receives a body portion of the endoscope. The sheath also includes a sleeve member joined to the sleeve housing to receive the endoscope shaft.

The sleeve member which depends from the sleeve housing has a predetermined length that is purposely of a shorter dimension than the length of the endoscope shaft to ensure that the terminal end of the endoscope shaft bottoms against a distal end cover of the sleeve member.

In one embodiment of the invention the sleeve member has an inner diameter sized to slidably accommodate the endoscope shaft such that an irrigation space is defined between the endoscope shaft and the sleeve member. One or more outlet ports in the distal cover of the sleeve communicate with the irrigation space. Thus irrigating solution that is directed into the irrigation space can flow through the outlet port(s) and across the distal cover to flush debris away from the viewing end of the endoscope.

In other embodiments of the invention the sleeve member which covers the viewing end of the endoscope includes one or more irrigation channels that are isolated from the endoscope shaft. Irrigating fluid exits the sleeve member from openings in the distal end cap or cover of the sleeve member to flush debris away from the distal end of the sleeve member and away from the viewing end of the endoscope shaft. In this manner the debris flushing action is accomplished without irrigation fluid contacting the endoscope shaft.

Since the terminal end of the endoscope shaft bottoms against the distal end of the sleeve member, the endoscope shaft is easily locatable in a predetermined position in the sleeve. Under this arrangement, a sleeve member of one length can be used with many different length endoscope shafts that are longer than the sleeve member.

If desired, the sleeve member of any embodiment of the invention can be provided with a distal end that is inclined at an angle of approximately 3° to 70° with respect to a longitudinal axis of the sleeve member.

The invention accordingly comprises the constructions and method hereinafter described, the scope of the invention being indicated in the claims.

DESCRIPTION OF THE DRAWINGS

In the accompanying drawings,

FIG. 3 is a fragmentary sectional view of a sleeve member that forms a part of the disposable endoscope sheath;

FIG. 4 is an end view of the sleeve member of FIG. 3; and

FIGS. 5–13 show further embodiments of the disposable sheath.

Corresponding reference characters indicate corresponding parts throughout the several views of the drawings.

DETAILED DESCRIPTION OF THE INVENTION

Figures 1, 2:
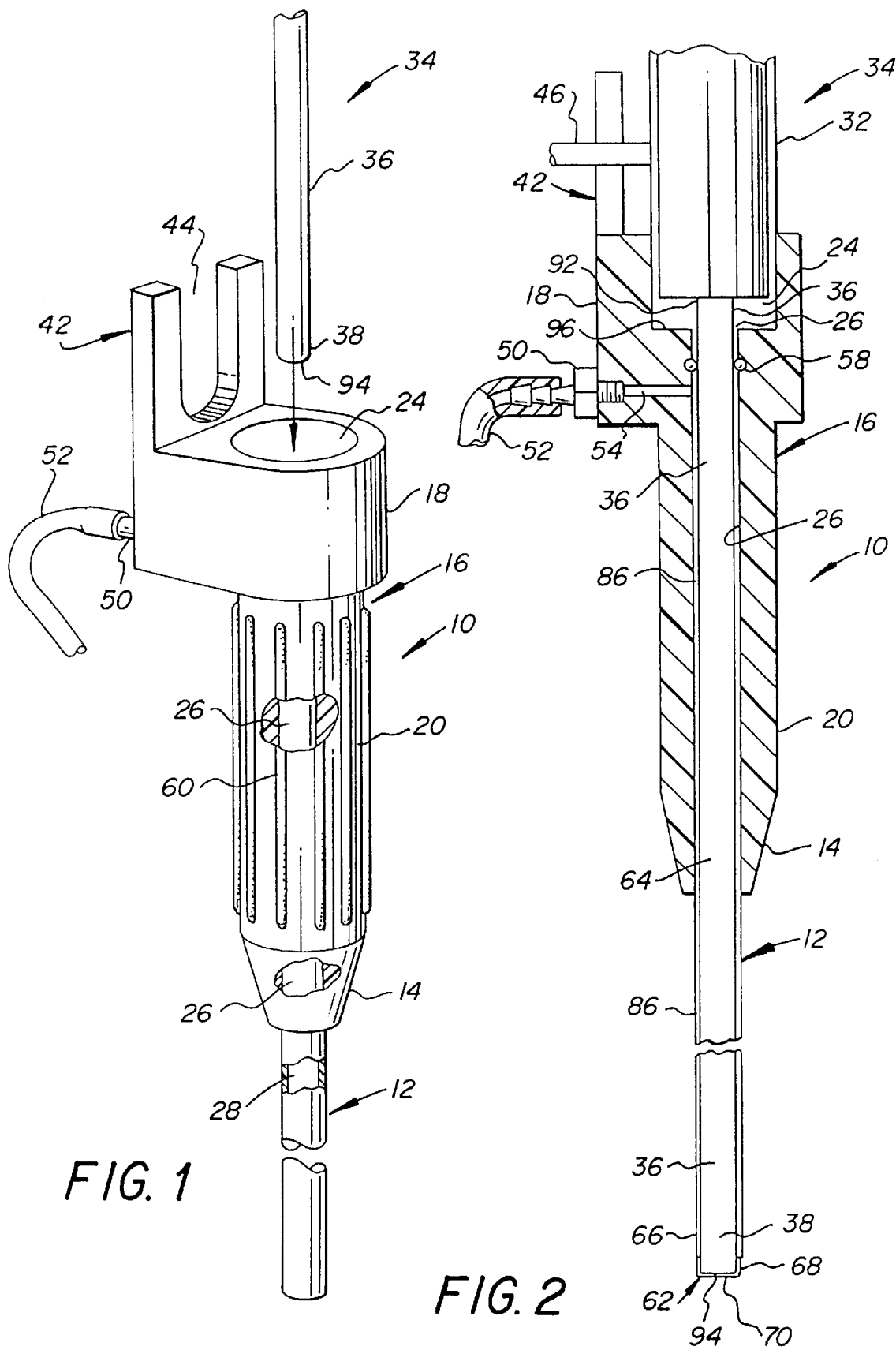
FIG. 1 is a simplified schematic perspective view of a disposable endoscope sheath incorporating one embodiment of the invention, including a sleeve housing and a sleeve member, prior to reception of an endoscope.
FIG. 2 is a sectional view thereof showing an endoscope in the sheath.

A disposable sheath incorporating one embodiment of the invention is generally indicated by the reference number 10 in FIG. 1.

The sheath 10 includes an elongated sleeve member 12 joined to an end portion 14 of a sleeve housing 16 that is preferably formed of a plastic such as acrylonitrile-butadiene-styrene. The sleeve housing 16 includes a collar portion 18 with a depending body portion 20 that facilitates handling of the sheath 10.

A recess 24 in the collar portion 18 communicates with a bore 26 in the body portion 20, the bore 26 communicating with the hollow interior 28 (FIG. 1) of the sleeve member 12. As shown in FIG. 2, the recess 24 is adapted to receive a housing 32 of an endoscope 34. A shaft 36 of the endoscope 34 is insertable in the bore 26 and in the hollow interior 28 of the sleeve member 12. The recess 24 can be of any shape that complements the shape of the endoscope housing 32.

Although not shown, the endoscope shaft 36 contains a light transmitting member and a lens, the lens being provided at a distal end portion 38 of the shaft 36.

The collar portion 18 further includes an upwardly extending yoke member 42 with a mouth 44 for securely holding the endoscope housing light port 46 to prevent rotation of the shaft 36.

An irrigation fitting 50 joined to the collar portion 18 supports an irrigation tube 52. The tube 52 communicates with the bore 26 in the body portion 20 through a fluid passage 54 in the collar portion 18. An O-ring 58 in the collar portion 18 is adapted to surround the endoscope shaft 36 to prevent fluid regression from the bore 26 into the recess 24. Grip assist elements 60 (FIG. 1) are formed on the body portion 20 to facilitate manual handling thereof.

The sleeve member 12 is a rigid structure of generally tubular shape preferably formed of thin-walled metal or plastic having a wall thickness of approximately 0.001 to 0.012 inches. A fully open proximal end 64 of the sleeve member 12 is bonded or otherwise secured within the bore 26 at the end 14 of the body portion 20 to form a leak-tight fit.

It should be noted that the body portion 20 primarily facilitates handling of the sheath 10 and, if desired, can be omitted to save material. Thus the sleeve member 12 can be joined directly to the collar portion 18, resulting in an abbreviated bore such as shown in the sheath 100 of FIG. 5.

Referring to FIGS. 3 and 4, a cup-shaped end cap 62 is provided at a distal portion 66 of the sleeve member 12. The end cap 62, which is preferably formed of plastic such as polycarbonate or polyvinyl chloride, includes an annular wall 68 and a base portion 70. The annular wall 68 is joined to an inner surface 72 of the sleeve member 12 in leak-tight fashion, in any suitable known manner. If desired, the annular wall 68 can be formed to a size that permits securance to the outside surface of the sleeve member 12 at the distal end portion 66. The base 70, which is preferably 0.001 to 0.007 inches thick, is formed of clear transparent optical grade plastic of the type described to permit an unobstructed field of view from the endoscope.

A series of three equally spaced discontinuous curved outlet slots 76, 78 and 80, are formed on a circular path in the base portion 70 proximate the annular wall 68 and have an angular extent of approximately 80° to 100°.

Although the number of outlet slots on the base portion 70 is preferably three, a lesser or greater number can be used, such as 1 to 10. The size and location of the slots are predetermined to avoid obscuring the field of view through the endoscope.

In using the disposable sheath 10, the distal end portion 38 of the endoscope shaft 36 is aligned with the recess 24 (FIG. 2) of the sleeve housing 16 and inserted through the bore 26 of the body portion 20 into the hollow interior 28 of the sleeve member 12.

The internal diameter of the bore 26, the sleeve 12 and the end cap 62 are of greater magnitude than the outside diameter of the endoscope shaft 36 by a predetermined amount of approximately 0.002 to 0.012 inches. In some instances the gap can increase to approximately 0.023 inches due to the draft required in a molded part. A substantially annular irrigation channel or space 86 is thus established at the periphery of the endoscope shaft 36 based on: (1) the diametrical difference between the bore 26 (FIG. 2) and the shaft 36, (2) the diametrical difference between the sleeve interior 28 and the shaft 36, and (3) the diametrical difference between the end cap 62 and the shaft 36. The irrigation channel 86 thus extends from the fluid passage 54 in the collar 18 (FIG. 2) to the base portion 70 of the end cap 62 and communicates with the curved outlet slots 76, 78 and 80 formed in the base portion 70.

Irrigation fluid such as saline is pumped or pulsed in any suitable known manner through the irrigation tube 52 to the fluid passage 54 and into the annular irrigation channel 86 for communication with the outlet slots 76, 78 and 80 of the sleeve member 12. Irrigation fluid can thus enter the irrigation channel 86 of the sleeve member 12 at the open proximal end 64 (FIG. 1).

As irrigation fluid is expelled through the outlet slots 76, 78 and 80, portions of the fluid pass across an outside end surface 88 of the base portion 70. The irrigation fluid passing across the outside end surface 88 thus flushes surgical debris from the surface 88 and away from the viewing end 94 of the endoscope shaft 36 to permit an unobstructed field of view from the distal end 38 of the endoscope shaft 36 through the base portion 70 of the end cap 62.

Referring to FIGS. 2 and 3, the length of the endoscope shaft 36 is measured from a proximal end 92 of the shaft 36 at the housing 32 to an opposite distal end 94 of the shaft 36 at the distal end portion 38. The distal end 94 is also referred to as the viewing end or the tip of the endoscope.

The disposable sheath 10 has a receiving length of predetermined magnitude for accommodating the endoscope shaft 36 within the bore 26 of the sleeve housing 16 and within the hollow interior 28 of the sleeve member 12. The receiving length of the sheath 10 for the endoscope shaft 36 is measured from a base 96 (FIG. 2) of the collar portion recess 24 to an inside end surface 74 (FIG. 3) of the sleeve member end cap 62.

The sheath 10 operates compatibly with the endoscope 32 when the endoscope shaft 36 is longer than the receiving length of the sheath 10. Thus, full insertion of the endoscope shaft 36 in the sheath 10 will cause the distal end 94 of the endoscope shaft 36 to bottom against the inside end surface 74 of the end cap 62 as shown in FIGS. 2 and 3. The sleeve member 12 can be easily formed to a predetermined length to ensure bottom engagement between the endoscope shaft and the sleeve member.

Engagement between the distal end 94 of the endoscope shaft 36 and the inside surface 74 is thus assured for endoscope shafts of different length provided such shafts are longer than the shaft receiving length of the sheath 10. Under this arrangement, the sheath 10 is intended for operation with endoscope shafts of different length, that exceed the receiving length of the sheath 10.

The slots 76, 78 and 80, which are outlets for irrigation fluid, also facilitate suction removal of a fluid droplet from the outside end surface 88 of the sleeve member 12. For example, in some instances a drop of irrigation fluid may be left at the outside end surface 88 of the sleeve member 12 when a flush cycle is completed. Since a field of view is taken through the outside end surface 88, a residual drop of irrigation fluid can impede the field of view through the endoscope. Thus a slight suction pulse at the irrigation tube 52 will draw the obscuring droplet of irrigation fluid from the outside end surface 88 back into the irrigation channel 86 through the slots 76, 78 and 80.

If desired, an anti-fogging coating can be provided at the end surface 88 of the sleeve 12 to help reduce retention time of the irrigation fluid.

The size of the irrigation channel 86, the wall thickness of the sleeve member 12 and the wall thickness of the end cap 62 are selected to provide a minimally intrusive low profile endoscope sheath for the endoscope shaft 36. Also, by limiting the size of the irrigation channel 86 to the specified size range, and particularly to a gap of approximately 0.001 to 0.003 inches along the length of the sleeve member 12, irrigation solution passing into the annular channel 86 tends to remain stationary when the pumping or pulsing of irrigation fluid at the irrigation tube 52 ceases. Thus irrigation fluid does not drip uncontrollably from the outlet slots 76, 78 and 80 when pumping activity ceases.

In accordance with the invention, the preferred size of the irrigation channel 86 is not intended to accommodate suction removal of surgical debris from the surgical site or from the terminal end 88 of the sleeve member 12. Suction removal of surgical debris generally requires a channel size that is sufficiently large to receive debris without blockage. Thus the size of a channel that is used for both suction removal of surgical debris and irrigation is normally large enough to permit irrigation fluid to drip from the channel when pumping of irrigation fluid ceases. Consequently, a channel that is used for both irrigation and for suction removal of surgical debris is often of a size that significantly increases the profile of the sheath and does not prevent involuntary dripping of irrigation fluid when pumping ceases. Such dripping can occur because of the formation of residual drops on the interior surfaces that eventually cascade.

To help control any flow or involuntary dripping of irrigation fluid from the sheath when irrigation pump activity ceases, some or all of the inner surface of the bore 26 and/or the sleeve member 12 can be optionally treated with a hydrophilic or other suitable coating to enhance retention of irrigation fluid. Alternatively, a fluid retention surface texture can be provided at the inner surface of the sheath 10 for fluid retention purposes.

For example, although not shown, a selected portion of the inner surface at the distal end 66 of the sleeve member 12 can include score marks, pits, protrusions, or an etched or rough surface to help capture residual solution in the irrigation channel 86 when irrigation pump activity ceases.

When an endoscopically assisted surgical procedure is completed, the entire sheath 10 can be discarded.

Another embodiment of the disposable sheath for an endoscope is generally indicated by the reference number 100 in FIGS. 5 and 6.

The sheath 100 includes a collar portion 102 with a depending adapter section 104. The sheath 100 also includes a sleeve member 110 elongated along an axis 112 and having a proximal end 114 joined to the adapter section 104 by press fit, thermowelding or by bonding with a suitable adhesive to form a leak-tight joint.

The collar portion 102 includes a recess 118 and a bore 120 for receiving an endoscope housing 122 and an endoscope shaft 124 of an endoscope 126. The sleeve member 110, which is generally circular in cross section, has a central endoscope receiving space 130 that aligns with the bore 120 to receive the endoscope shaft 124.

The collar portion 102 is formed with an inlet fluid passage 130 that joins a circular fluid duct 134 having two depending feeder portions 136 and 138. The feeder portions 136 and 138 align with sleeve member irrigation channels 140 and 142 at an inlet end of the irrigation channels.

The irrigation channels 140 and 142 which are similar in size and shape to the feeder portions 136 and 138, are formed in an annular marginal wall 144 of the sleeve member 110. The irrigation channels 140 and 142 are oppositely disposed and have angular extents of approximately 100° to 160° to match the angular extent of the feeder portions 136 and 138. In addition, the irrigation channels 140 and 142 are isolated from the bore 120 and the endoscope receiving space 130.

A plastic end cover 150 of transparent optical grade quality is joined to a distal end 152 of the sleeve member 110 by bonding with a suitable biocompatible adhesive or by thermowelding. The end cover 150 is formed with outlet openings 154 and 156 that align with and match the size of the irrigation channels 140 and 142.

It should be noted that although the sleeve member 110 includes two irrigation channels 140 and 142, a lesser or greater number can be used such as one to ten.

In using the sheath 100, the endoscope shaft 124 is inserted into the bore 120 of the collar portion 102 and in the endoscope receiving space 130 of the sleeve member 110 in a manner similar to that described for the sheath 10.

The inner diameter of the bore 120 is approximately 0.001 to 0.008 inches larger in diameter than the endoscope shaft 124. The endoscope receiving length of the sheath 100, and more particularly the sleeve member 110, is sized to permit a terminal end 158 of the endoscope shaft 124 to bottom against an inner surface 160 of the end cover 150. The width of the irrigation channels 140 and 142 along a cross-sectional diameter of the sleeve member is approximately 0.002 to 0.006 inches.

Irrigating fluid is pulsed or pumped into the irrigation channels 140 and 142 via the inlet fluid passage 130, the circular duct 134 and the feeder portions 136 and 138 that communicate with the irrigation channels 140 and 142. Irrigation fluid exits from the sleeve member at the outlet openings 154 and 156 in the end cover 150. The irrigation fluid, as it exits from the outlet openings 154 and 156, can flow onto an outside end surface 162 of the end cover 150 and flush surgical debris from the end surface 162 and away from the viewing end 158 of the endoscope shaft 124 thus providing an effective cleaning action.

Since the irrigation channels 140 and 142 are isolated from the endoscope receiving space 130 and the endoscope shaft 124, there is no contact between the irrigation fluid and the endoscope shaft 124. Furthermore, the endoscope shaft 124 is entirely shielded by the sleeve member 110 from the surgical environment. Under this arrangement, the endoscope shaft 124 is not contaminated by the surgical environment and can be reused without the need to clean, if desired, whereas the sheath 100 is conveniently disposable.

The flow rate of irrigation fluid through the irrigation channels 140 and 142 can be adjusted in accordance with surgical requirements by manipulation of a control setting (not shown) that controls the flow of such fluid through the inlet fluid passage 130. The flow of irrigation fluid can be a continuous pulsing action, a continuous flow, or a selective forward then reverse pump action as desired.

Figure 7:
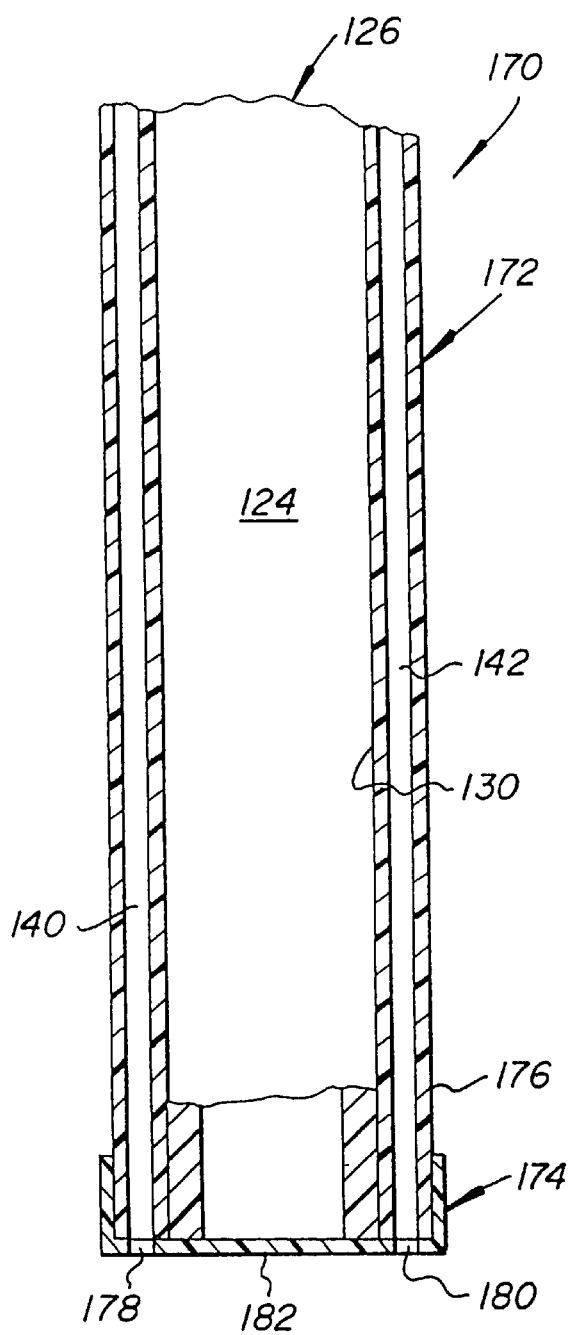
Figure 8:
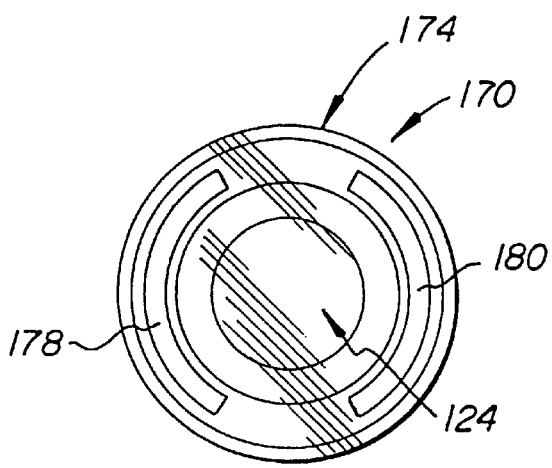

A further embodiment of the disposable sheath for an endoscope is generally indicated by the reference number 170 in FIGS. 7 and 8. The sheath 170 includes a sleeve member 172 joined to a collar portion (not shown) that is identical to the collar portion 102 of the sheath 100.

The primary difference between the sheath 170 and the sheath 100 is a cup shaped end cap 174 rather than the disk shaped end cover 150 of the sheath 100.

The cup shaped end cap 174 is joined to a distal end portion 176 of the sleeve member 172 in any suitable known manner as by bonding or thermowelding.

The cup shaped end cap 174 includes outlet openings 178 and 180 identical to the outlet openings 154 and 156 of the end cover 150. The outlet openings 178 and 180 align with and match the size of the sleeve member irrigation channels 140 and 142.

The sheath 170 operates in a manner similar to that described for the sheath 100 to provide a flushing action at an outside end surface 182 of the cup shaped end cap 174. As with the sheath 100, the endoscope shaft 124 in the sheath 170 is isolated from the irrigation channels 140 and 142 and shielded from the surgical environment.

Since there is no communication between the endoscope receiving space 130 of the sheath 170 and the irrigation channels 140 and 142, the endoscope 126 can be reused without cleaning, if desired, whereas the sheath 170 is conveniently disposable after use.

Although the number of irrigation channels in the sheath 170 is two, a lesser or greater number can be used such as one to ten channels.

Figure 9:
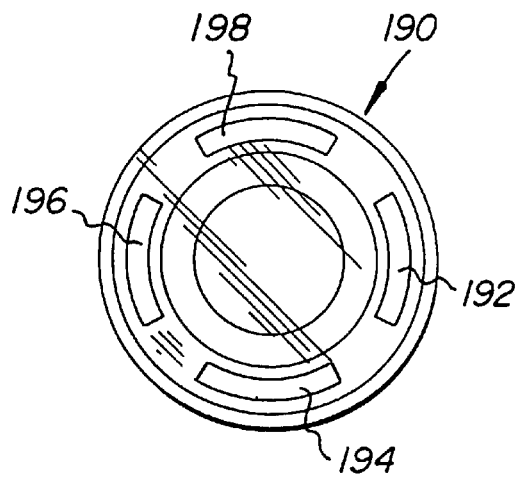

Thus a further embodiment of the sheath indicated by reference number 190 in FIG. 9 includes four equally spaced irrigation channels (not shown) that match the size and shape of the irrigation outlet openings 192, 194, 196 and 198. The structure of the sheath 190 is based on the structural principles of the sheath 100; and operation of the sheath 190 is otherwise similar to that of the sheath 100.

Figure 10:
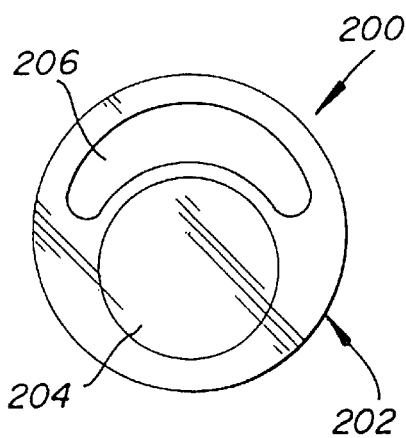

Another embodiment of the disposable sheath, wherein the endoscope receiving space does not communicate with the irrigation space, is generally indicated by the reference number 200 in FIG. 10. The sheath 200 is shown in end view only for purposes of simplicity, but conforms with the general structural scheme of the sheath 170.

Thus the sheath 200 includes a cup shaped end cap 202 having an optically clear field of view portion 204 for an endoscope receiving space of a corresponding sleeve member (not shown) that is based on the structural principles of the sheath 100. The end cap 202 also includes a single irrigation outlet opening 206 which matches the shape and size of a single irrigation channel in the corresponding sleeve member (not shown).

Although the collar member of the sheath 200 is not shown, it has a single feeder passage similar in size to that of the irrigation outlet opening 206. The feeder passage feeds incoming irrigation fluid into the sleeve member irrigation channel for outflow at the irrigation outlet opening 206 to flush debris from the field of view portion 204 of the end cap 202.

The sheath 200 is operationally similar to the sheath 170.

Figure 11:
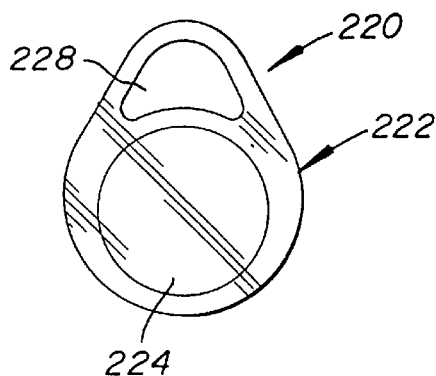

A further embodiment of the disposable sheath with non-communication between the irrigation channel and the endoscope space is generally indicated by reference number 220 in FIG. 11. The sheath 220 includes a cup-shaped end cap 222 that is pear-shaped in cross section rather than circular. The outer periphery of the sleeve member (not shown) is correspondingly pear-shaped and has an endoscope receiving space (not shown) corresponding to a field of view portion 224 of the end cap 222. The sleeve member (not shown) also includes a single irrigation channel of corresponding size and shape with the single irrigation outlet port 228 of the end cap 222. The sheath 220 has a collar portion of complementary shape with respect to the sleeve member based on the structural principles of the sheath 100, and operates in a manner similar to that previously described for the sheaths 170 and 200.

Figure 13:
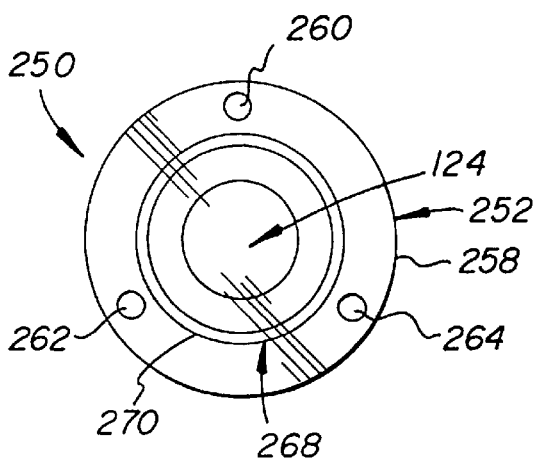
Figure 12:
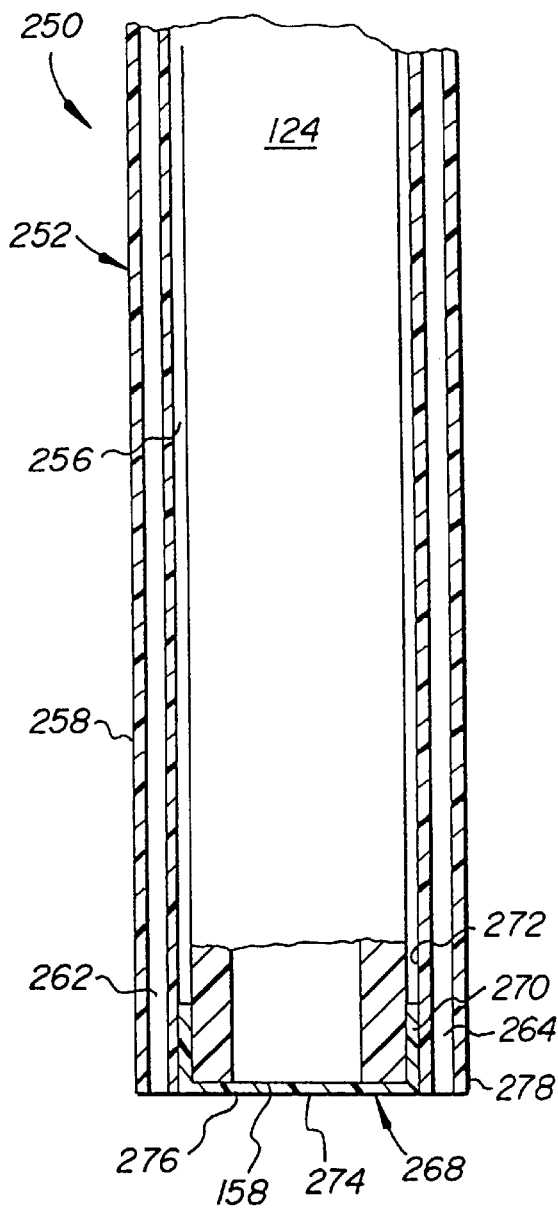

Still another embodiment of a disposable sheath for an endoscope is generally indicated by the reference number 250 in FIGS. 12 and 13.

The sheath 250 includes a sleeve member 252 and a collar portion that is not shown for purposes of simplicity but follows the general structural concepts of the sheath 100.

The sleeve member 252 includes an endoscope receiving space 256 surrounded by an annular wall 258 having three equally spaced irrigation channels 260, 262 and 264. There is no communication between the endoscope receiving space 256 and the irrigation channels 260, 262 and 264. The irrigation channels 260, 262 and 264 each have a diameter of approximately 0.004 to 0.012 inches and although the number of irrigation channels is shown as three, there can be a lesser or greater amount such as two to ten.

A cup shaped distal end cap 268 is secured in the endoscope receiving space 256 by bonding a cylindrical wall 270 of the end cap 268 to an inner wall surface 272 of the endoscope receiving space. An outer end face 274 on an optically clear base 276 of the end cap 268 can be flush with a distal end 278 of the sleeve member 252 or slightly recessed. Suitable clearances between (1) the endoscope shaft 124 and the end cap wall 270, and (2) between the endoscope shaft 124 and the endoscope receiving space 256, such as specified for the sheath 100, are provided for the sheath 250.

In using the sheath 250, irrigation fluid is pulsed or pumped into the irrigation channels 260, 262 and 264 in a manner similar to that previously described for the sheath 100. The irrigation fluid is expelled from the irrigation channels 260, 262 and 264 at the distal end 278 of the sleeve member 252 and can flow onto the outer end face 274 of end cap 268 thereby flushing surgical debris from the end face 274 and away from the viewing end 158 of the endoscope shaft 124 to provide an effective cleaning action.

As described for the sheaths 100 and 170, for example, the endoscope shaft 124 is entirely shielded from the surgical environment and can thus be reused without cleaning whereas the sheath 250 can be conveniently disposed of after use.

It should be noted that the end portions of the sleeve members of any of the disclosed embodiments including the end caps and end covers can be inclined at an angle of approximately 0° to 70° to the longitudinal axis of the sleeve member. It should also be noted that disk-shaped end caps can be substituted for cup-shaped end caps and vice-versa.

Some advantages of the invention evident from the foregoing description include a disposable sheath that has a low profile structure. Thus the emplacement of the endoscope sheath in a surgical zone does not require any significant enlargement of a surgical incision to accommodate the sleeve shrouded endoscope. The sleeve member of the sheath is disposable and can permit reuse of the endoscope if complete shielding from the surgical environment is provided by the sheath. A further advantage of the disposable sheath is the effective flushing action to clean debris away from the viewing end of the endoscope without requiring contact between the irrigation fluid and the endoscope. Still another advantage is that the sleeve member need not be customized to different lengths of an endoscope but can accommodate a variety of different endoscope lengths that are longer than the sleeve member. The disposable endoscope sheath is economical to manufacture and saves time and money by the convenient installation and removal of the endoscope shaft.

In view of the above, it will be seen that the several objects of the invention are achieved and other advantageous results attained.

As various changes can be made in the above constructions without departing from the scope of the invention, it is intended that all matter contained in the above description or shown in the accompanying drawings shall be interpreted as illustrative and not in a limiting sense.

What is claimed is:

1. A disposable sheath for an endoscope having an endoscope shaft with a viewing end through which a field of view is taken and with a cross sectional size; the disposable sheath comprising:
   a) a disposable elongated sleeve having an elongated wall defining an endoscope receiving space having a cross sectional size larger than the cross sectional size of the endoscope shaft so as to accommodate the endoscope shaft therein and define an irrigation space of annular cross section area having a radial extent between said elongated wall and the endoscope shaft,
   b) said sleeve having a distal end closed by a distal end cover and being of predetermined length to enable said distal end cover to engage the viewing end of the endoscope shaft when the endoscope shaft is in said endoscope receiving space, said distal end cover defining a plurality of irrigation outlet openings and having an optically clear portion to provide a clear field of view through said distal end cover from the viewing end of the endoscope shaft, said optically clear portion having an outside surface,
   c) said sleeve being self supporting, non-inflatable, non-expandable and said annular cross section area being sized to ensure that irrigation solution passing into said irrigation space does not drip uncontrollably from said irrigation outlet openings defined by said distal end cover of said sleeve when the flow of irrigation solution is stopped,
   d) said irrigation outlet openings being equally spaced around said optically clear portion and communicating with said irrigation space such that irrigation solution directed into said irrigation space can flow out of said irrigation outlet openings and onto said outside surface of said distal end cover to flush surgical debris from said outside surface of said distal end cover and away from the viewing end of the endoscope shaft to provide a clear field of view from the viewing end of the endoscope shaft.

2. The disposable sheath as claimed in claims 1 wherein said sleeve is generally circular in cross section.

3. The disposable sheath as claimed in claim 1 wherein said irrigation outlet openings are formed in a circular arrangement.

4. The disposable sheath as claimed in claim 1 wherein said distal end cover is disk shaped.

5. The disposable sheath as claimed in claim 1 wherein said distal end cover is cup shaped.

6. The disposable sheath as claimed in claim 5 wherein said sleeve has an inside surface and said cup shaped distal end cover has an annular wall secured to said inside surface of said sleeve.

7. The disposable sheath as claimed in claim 5 wherein said sleeve has an outside surface and said cup shaped distal end cover has an annular wall secured to said outside surface of said sleeve.

8. The disposable sheath as claimed in claim 1 wherein said sleeve is sized to define a selected radial extent of approximately 0.001 to 0.003 inch between the endoscope shaft and said elongated wall of said sleeve.

9. A disposable sheath for an endoscope comprising
   a) a sleeve having an elongated wall defining an endoscope receiving space sized to accommodate an endoscope shaft with a distal viewing end through which a field of view is taken from the endoscope,
   b) said sleeve having a distal end and a distal end cover affixed to said distal end to enclose said endoscope receiving space, said sleeve being of predetermined length to enable said distal end cover to engage the viewing end of the endoscope shaft when the endoscope shaft is in said endoscope receiving space, said distal end cover of said sleeve having an optically clear distal portion to provide a clear field of view through said distal end cover from the viewing end of the endoscope shaft, said optically clear distal portion having an outside distal surface,
   c) said elongated wall being formed with an irrigation channel, non-communicable with said endoscope receiving space, said irrigation channel having an inlet portion and a plurality of equally spaced irrigation outlet openings formed in a circular arrangement and positioned proximate said optically clear distal portion of said end cover, such that irrigation solution passing into said irrigation channel does not drip uncontrollably from said irrigation outlet openings when the flow of irrigation solution is stopped and irrigation solution directed into said inlet portion of said irrigation channel can flow out of said irrigation outlet openings and onto said outside distal surface of said optically clear distal portion to flush surgical debris away from said outside distal surface of said optically clear distal portion and away from the viewing end of the endoscope shaft to provide a clear field of view from the viewing end of the endoscope shaft.

10. The disposable sheath as claimed in claim 9 wherein said distal end cover is disk shaped.

11. The disposable sheath as claimed in claim 10 wherein said distal end cover has at least one irrigation outlet opening.

12. The disposable sheath as claimed in claim 10 wherein said distal end cover has a plurality of irrigation outlet openings.

13. The disposable sheath as claimed in claim 12 wherein said irrigation outlet openings are formed in a circular arrangement.

14. The disposable sheath as claimed in claim 9 wherein said distal end cover is cup shaped.

15. The disposable sheath as claimed in claim 14 wherein said distal end cover has at least one irrigation outlet opening.

16. The disposable sheath as claimed in claim 15 wherein said distal end cover has a plurality of irrigation outlet openings.

17. The disposable sheath as claimed in claim 16 wherein said irrigation outlet openings are equally spaced and formed in a circular arrangement.

18. The disposable sheath as claimed in claim 9 wherein said sleeve is generally circular in cross section.

19. The disposable sheath as claimed in claim 9 wherein said sleeve is non-circular in cross section.

* * * * *